United States Patent [19]

Sasaki

[11] Patent Number: 4,777,296

[45] Date of Patent: Oct. 11, 1988

[54] STYRYL DERIVATIVES AND ELECTROPHOTOGRAPHIC PHOTOCONDUCTOR COMPRISING ONE STYRYL DERIVATIVE

[75] Inventor: Masaomi Sasaki, Susono, Japan

[73] Assignee: Ricoh Company, Ltd., Tokyo, Japan

[21] Appl. No.: 857,180

[22] Filed: Apr. 29, 1986

Related U.S. Application Data

[62] Division of Ser. No. 702,072, Feb. 15, 1985, Pat. No. 4,606,988.

[30] Foreign Application Priority Data

Feb. 21, 1984 [JP] Japan .................................. 59-29606

Feb. 21, 1984 [JP] Japan .................................. 59-29607

[51] Int. Cl.[4] ............................................. C07C 87/54

[52] U.S. Cl. .................................... 564/433; 564/315; 564/427; 564/428; 564/430; 564/434; 558/418; 560/43; 562/457

[58] Field of Search ............... 564/315, 427, 428, 430, 564/433, 434; 558/418; 562/457; 560/43

[56] References Cited

U.S. PATENT DOCUMENTS 4,263,456 4/1981 Rogers ................................ 564/315

4,562,131 12/1985 Sasaki et al. ........................ 534/689

FOREIGN PATENT DOCUMENTS 2121789 1/1984 United Kingdom .

*Primary Examiner*—Glennon H. Hollrah

*Assistant Examiner*—John A. Sopp

*Attorney, Agent, or Firm*—Oblon, Fisher, Spivak, McClelland & Maier

[57] ABSTRACT

Styryl derivatives of the formula

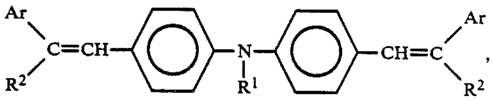

and an electrophotographic photoconductor comprising an electroconductive support material and a photosensitive layer comprising at least one styryl derivative of the same formula are disclosed, in which $R^1$ is selected from the group consisting of an alkyl group, a substituted alkyl group, an aryl group and substituted aryl group; $R^2$ is selected from the group consisting of hydrogen, an alkyl group, a substituted alkyl group, an aryl group and a substituted aryl group; and Ar represents an aryl group or a substituted aryl group.

2 Claims, 2 Drawing Sheets

STYRYL DERIVATIVES AND ELECTROPHOTOGRAPHIC PHOTOCONDUCTOR COMPRISING ONE STYRYL DERIVATIVE

This is a division of application Ser. No. 702,072, filed Feb. 15, 1985, now U.S. Pat. No. 4,606,988.

BACKGROUND OF THE INVENTION

The present invention relates to styryl derivatives and an electrophotographic photoconductor comprising a photosensitive layer containing one styryl derivative overlayed on an electroconductive support material.

Conventionally, a variety of inorganic and organic electrophotographic photoconductors are known. As inorganic photoconductors for use in electrophotography, there are known types, in which the photoconductive material is, for instance, selenium, cadmium sulfide and zinc oxide. In an electrophotographic process, a photoconductor is first exposed to corona charges in the dark, so that the surface of the photoconductor is electrically charged uniformly. The thus uniformly charged photoconductor is then exposed to original light images and the portions exposed to the original light images selectively become electroconductive so that electric charges dissipate from the exposed portions of the photoconductor, whereby latent electrostatic images corresponding to the original light images are formed on the surface of the photoconductor. The latent electrostatic images are then developed by the so-called toner which comprises a colorant, such as a dye or a pigment, and a binder agent made, for instance, of a polymeric material; thus, visible developed images can be obtained on the photoconductor. It is necessary that photoconductors for use in electrophotography have at least the following fundamental properties: (1) chargeability to a predetermined potential in the dark; (2) minimum electric charge dissipation in the dark; and (3) quick dissipation of electric charges upon exposure to light.

While the above-mentioned inorganic electrophotographic photoconductors have many advantages over other conventional electrophotographic photoconductors, at the same time they have several shortcomings from the viewpoint of practical use.

For instance, a selenium photoconductor, which is widely used at present, has the shortcoming that its production is difficult and, accordingly, its production cost is high. Further, it is difficult to work it into the form of a belt due to its poor flexibility, and it is so vulnerable to heat and mechanical shocks that it must be handled with the utmost care.

Cadmium sulfide photoconductors and zinc oxide photoconductors are prepared by dispersing cadmium sulfide or zinc oxide in a binder resin. They can be produced inexpensively compared with selenium photoconductors and are commonly used in practice. However, the cadmium sulfide and zinc oxide photoconductors are poor in surface smoothness, hardness, tensile strength and wear resistance. Therefore, they are not suitable as photoconductors for use in plain paper copiers in which the photoconductors are used in quick repetition.

Recently, organic electrophotographic photoconductors, which are said not to have such shortcomings of the inorganic electrophotographic photoconductors, have been proposed, and some of them are in fact employed for practical use. Representative examples of such organic electrophotographic photoconductors are an electrophotographic photoconductor comprising poly-N-vinylcarbazole and 2,4,7-trinitro-fluorene-9-one (U.S. Pat. No. 3,484,237); a photoconductor in which poly-N-vinylcarbazole is sensitized by a pyrylium salt type coloring material (Japanese Patent Publication No. 48-25658); a photoconductor containing as the main component an organic pigment (Japanese Laid-Open Patent Application No. 47-37543); and a photoconductor containing as the main component an eutectic crystaline complex (Japanese Laid-Open Patent Application No. 47-10735).

Although the above-mentioned organic electrophotographic photoconductors have many advantages over other conventional electrophotographic photoconductors, they still have several shortcomings from the viewpoint of practical use, in particular, for use in high speed copying machines, in terms of cost, production, durability and electrophotographic sensitivity.

SUMMARY OF THE INVENTION

It is therefore an object of the present invention to provide styryl derivatives which are useful as organic photoconductive materials for electrophotography and an electrophotographic photoconductor or element comprising a photosensitive layer containing at least one of such styryl derivatives overlayed on an electroconductive support material, with high photosensitivity, which does not give rise to difficulties in producing the electrophotographic photoconductor, and which is comparatively inexpensive and excellent in durability.

The styryl derivatives employed in the present invention are represented by the following general formula (I):

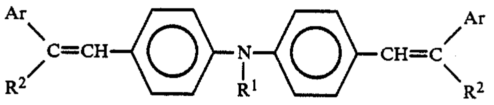

(I)

wherein $R^1$ is selected from the group consisting of an alkyl group, a substituted alkyl group, an aryl group and a substituted aryl group; $R^2$ is selected from the group consisting of hydrogen, an alkyl group, a substituted alkyl group, an aryl group and a substituted aryl group; and Ar represents an aryl group or a substituted aryl group.

DETAILED DESCRIPTION OF THE PREFERRED EMBODIMENTS

Figure 1:
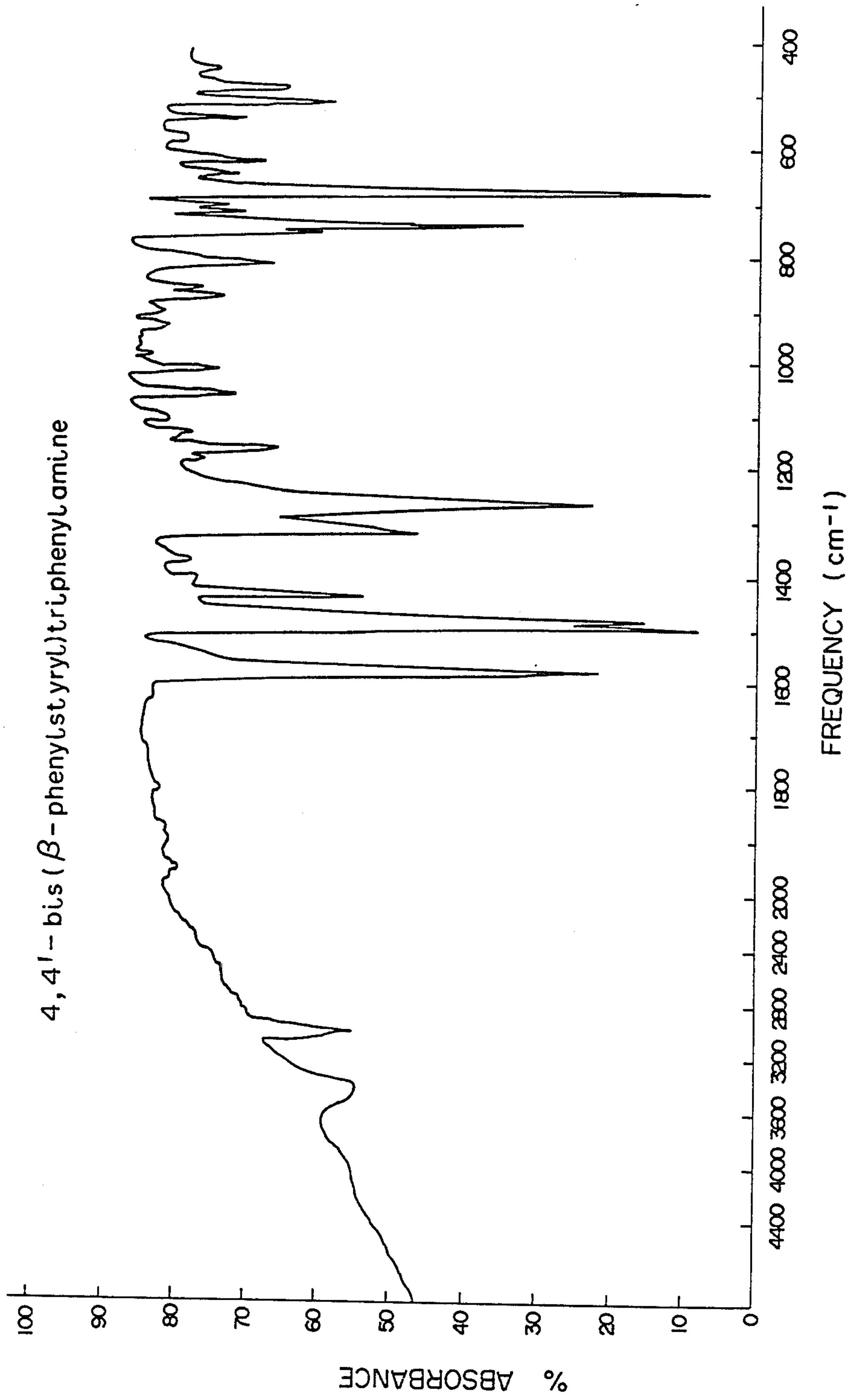
FIG. 1 is an infrared spectrum of 4,4′-bis(β-phenylstyryl)triphenylamine.

The styryl derivatives of the formula (I) for use in the present invention can be prepared by reacting a phosphorus derivative of formula (II) with an aldehyde derivative of formula (III) in the presence of a basic catalyst at temperatures ranging from room temperature to about 100° C.:

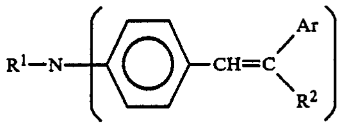
(I)

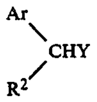
(II)

wherein Y represents a phosphonium group of the formula

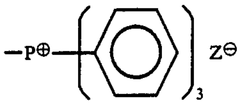

in which $Z^{\ominus}$ indicates a halogen ion; or a dialkoxyphosphorous group of the formula $-PO(OR)_2$ in which R indicates a lower alkyl group.

(III)
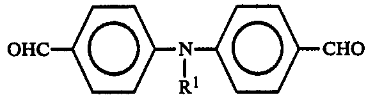

wherein $R^1$ represents an alkyl group, a substituted alkyl group, an aryl group or a substituted aryl group.

In the above formulas, the aryl group is selected from the group consisting of a phenyl group, a styryl group, a biphenylyl group, a naphthyl group and an anthryl group; and the substituted aryl group have at least one substituent selected from the group consisting of an alkyl group, an alkoxy group, an aryloxy group, halogen, a dialkylamino group, a hydroxy group, a carboxy group and esters thereof, a nitro group, an acetyl group and a cyano group.

As the basic catalyst for the abqve reaction, sodium, hydroxide, potassium hydroxide, sodium amide, sodium hydride, and alcoholates such as sodium methylate and potassium tert-butoxide, can be employed.

As the reaction solvent, the methanol, ethanol, isopropanol, butanol, 2-methoxyethanol, 1,2-dimethoxyethane, bis(2-methoxyethyl)ether, dioxane, tetrahydrofuran, toluene, xylene, dimethyl sulfoxide, N,N-dimethylformamide, N-methylpyrrolidone and 1,3-dimethyl-2-imidazolidinone can be employed.

Of the above solvents, polar solvents, for example, N,N-dimethylformamide and dimethyl sulfoxide are particularly suitable for this reaction.

The reaction temperature for the above reaction can be set in a relatively wide range, depending upon (i) the stability of the solvent employed in the presence of the basic catalyst, (ii) the reactivities of the condensation components, that is, the phosphorous derivative of the formula (II) and the aldehyde derivative of the formula (III), and (iii) the properties of the basic catalyst which works as a condensation agent in this reaction. When a polar solvent is employed as the reaction solvent, the reaction temperature can be set in the range of room temperature to about 100° C., more preferably in the range of room temperature to about 80° C. However, if it is desired to shorten the reaction time or when a less reactive condensation agent is employed, the reaction temperature can be elevated beyond the aforementioned range.

As the sensitizer dye, the following can be employed in the present invention: Triarylmethane dyes, such as Methyl Violet, Crystal Violet; xanthene dyes, such as Rose Bemgale, Erythrosin, Rhodamine B, azine dyes, such as Methylene Blue; 2,4,7-trinitro-9-fluorenone, 2,4-dinitro-9-fluorenone.

As organic pigments, the following can be employed in the present invention: azo dyes, such as C.I. Pigment Blue 25 (C.I. 21180), C.I. Pigment Red 41 (C.I. 21200), and C.I. Basic Red 3 (C.I. 45210); a phthalocyanine-type pigment, such as C.I. Pigment Blue 16 (C.I. 74100); Indigo-type pigments, such as C.I. Vat Brown 5 (C.I. 73410) and C.I. Violet Dye (C.I. 73030); and perylene-type pigments, such as Algo Scarlet B and Indanthrene Scarlet R; and inorganic pigments, such as selenium, a selenium-tellenium alloy, cadmium sulfide and amorphous silicon can be also employed.

In the electrophotographic photoconductor according to the present invention, at least one or more styryl derivatives having the previously described formula (I) is contained in the photosensitive layer. The styryl derivatives can be employed in different ways, for example, as shown in FIG. 2, FIG. 3 and FIG. 4.

Figure 2:
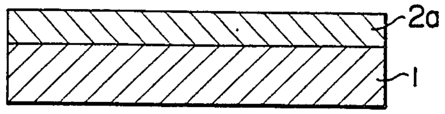
FIG. 2 is an enlarged schematic cross-sectional view of an embodiment of an electrophotographic photoconductor according to the present invention.

In the photoconductor as shown in FIG. 2, a photosensitive layer 2a is formed on an electroconductive support material 1, which photosensitive layer 2a comprises a styryl derivative, a sensitizer dye and a binder agent. In this photoconductor, the styryl derivative works as photoconductor material through which charge carriers are generated and transported. The generation and transportation of charge carrier are necessary for the light decay of the photoconductor. However, the styryl derivatives scarcely absorb light in the visible light range and, therefore, it is necessary to sensitize the derivatives by adding a sensitizer dye which absorbs light in the visible light range in order to form latent electrostatic images on the photoconductor by use of visible light.

Figure 3:
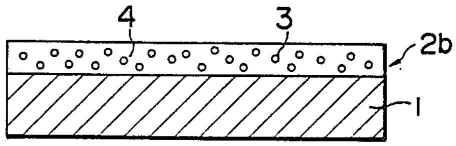
FIG. 3 is an enlarged schematic cross-sectional view of another embodiment of an electrophotographic photoconductor according to the present invention.
Figure 4:
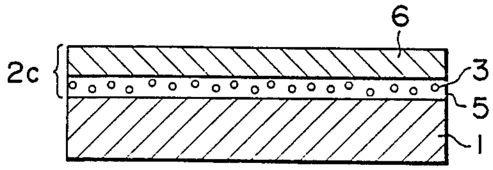
FIG. 4 is an enlarged schematic cross-sectional view of a further embodiment of an electrophotographic photoconductor according to the present invention.

Referring to FIG. 3, there is shown an enlarged cross-sectional view of another embodiment of an electrophotographic photoconductor according to the present invention.

In the figure, on the electroconductive support material 1, there is formed a photosensitive layer 2b comprising a charge generating material 3 dispersed in a charge transporting medium 4 which comprises a styryl derivative or and a binder agent (or a binder agent and a plasticizer). In this embodiment, the styryl derivative and the binder agent in combination constitute the charge transporting medium 4. The charge generating material 3, which is, for example, an inorganic or organic pigment, generates charge carriers. The charge transporting medium 4 mainly serves to accept the charge carriers generated by the charge generating material 3 and to transport those charge carriers.

In this electrophotographic photoconductor, it is a basic requirement that the light-absorption wavelength regions of the charge generating material 3 and the styryl derivative not overlap in the visible light range. This is because, in order that the charge generating material 3 produce charge carriers efficiently, it is necessary that light pass through the charge transporting medium 4 and reach the surface of the charge generating material 3. Since the styryl derivatives of the formula (I) do not substantially absorb light in the visible range, they can work effectively as charge transporting materials in combination with the charge generating material 3 which absorbs the light in the visible region and generates charge carriers.

Referring to FIG. 4, there is shown an enlarged cross-sectional view of a further embodiment of an electrophotographic photoconductor according to the present invention. In the figure, there is formed on the electroconductive support material 1 a two-layered photosensitive layer 2*c* comprising a charge generating layer 5 consisting essentially of the charge generating material 3, and a charge transporting layer 6 containing a styryl derivative of the formula (I).

In this photoconductor, light which has passed through the charge transporting layer 6 reaches the charge generating layer 5, so that charge carriers are generated within the charge generating layer 5 in the region which the light has reached. The charge carriers which are necessary for the light decay for latent electrostatic image formation are generated by the charge generating material 3, accepted and transported by the charge transporting layer 6. In the charge transporting layer 6, the styryl derivative mainly works for transporting charge carriers. The generation and transportation of the charge carriers are performed in the same manner as that in the photoconductor shown in FIG. 3.

When the electrophotographic photoconductor according to the present invention as shown in FIG. 2 is prepared, one or more of the above prepared styryl derivatives is dispersed in a binder resin solution, and a sensitizer dye is then added to the mixture, and the thus prepared photosensitive liquid is applied to an electroconductive support material 1 and dried, so that a photosensitive layer 2*a* is formed on the electroconductive support material 1.

It is preferable that the thickness of the photosensitive layer 2*a* be in the range of about 3 μm to about 50 μm, more preferably in the range of about 5 μm to about 20 μm. It is preferable that the amount of the styryl derivative contained in the photosensitive layer 2*a* be in the range of about 30 wt.% to about 70 wt.% of the total weight of the photosensitive layer 2*a*, more preferably about 50 wt.% of the total weight of the photosensitive layer 2*a*. Further, it is preferable that the amount of the sensitizer dye contained in the photosensitive layer 2*a* be in the range of about 0.1 wt.% to about 5 wt.% of the total weight of the photosensitive layer 2*a*, more preferably in the range of about 0.5 wt.% to about 3 wt.%, of the total weight of the photosensitive layer 2*a*.

As the sensitizer dye, the following can be employed in the present invention: Triarylmethane dyes, such as Brilliant Green, Victoria Blue B, Methyl Violet, Crystal Violet, and Acid Violet 6B; xanthene dyes, such as Rhodamine B, Rhodamine 6G, Rhodamine G Extra, Eosin S, Erythrosin, Rose Bengale, and Fluorescein; thiazine dyes such as Methylene Blue; cyanin dyes such as cyanin; and pyrylium dyes, such as 2,6-diphenyl-4-(N,N-dimethylaminophenyl)thiapyrylium perchlorate and benzopyrylium salt (as described in Japanese Patent Publication 48-25658). These sensitizer dyes can be used alone or in combination.

An electrophotographic photoconductor according to the present invention as shown in FIG. 3 can be prepared, for example, as follows. A charge generating material 3 in the form of small particles is dispersed in a solution of one or more styryl derivatives and a binder agent. The thus prepared dispersion is applied to the electroconductive support material 1 and is then dried, whereby a photosensitive layer 2*b* is formed on the electroconductive support material 1.

It is preferable that the thickness of the photosensitive layer 2*b* be in the range of about 3 μm to about 50 μm, more preferably in the range of about 5 μm to about 20 μm. It is preferable that the amount of the styryl derivative contained in the photosensitive layer 2*b* be in the range of about 10 wt.% to about 95 wt.%, more preferably in the range of about 30 wt.% to about 90 wt.% of the total weight of the photosensitive layer 2*b*. Further, it is preferable that the amount of the charge generating material 3 contained in the photosensitive layer 2*b* be in the range of about 0.1 wt.% to about 50 wt.%, more preferably in the range of about 1 wt.% to about 20 wt.%, of the total weight of the photosensitive layer 2*b*.

As the charge generating material 3, the following can be employed in the present invention: inorganic pigments, such as selenium, a selenium-tellurium alloy, cadmium sulfide, a cadmium sulfide-selenium alloy, and amorphous-silicon; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo dye having a distyrylbenzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), an azo dye having a distyryl carbazole skeleton (Japanese Laid-Open Patent Application 54-14967); a phthalocyanine-type pigment such as C.I. Pigment Blue 16 (C.I. 74100); Indigo-type pigments such as C.I. Vat Brown 5 (C.I. 73410) and C.I. Vat Dye (C.I. 73030); and perylene-type pigments, such as Algo Scarlet B (made by Bayer Co., Ltd.) and Indanthrene Scarlet R (made by Bayer Co., Ltd). These charge generating materials can be used alone or in combination.

The photoconductor according to the present invention as shown in FIG. 4 can be prepared, for example, as follows. A charge generating material 3 is vacuum-evaporated on the electroconductive support material 1, or a charge generating material 3 in the form of fine particles is dispersed in a solution of a binder agent. This dispersion is applied to the electroconductive support material 1 and then dried, and, if necessary, the applied layer is subjected to buffing to make the surface smooth or to adjust the thickness of the layer to a predetermined thickness, whereby a charge generating layer 5 is formed. A charge transporting layer 6 is then formed on the charge generating layer 5 by applying a solution of one or more styryl derivatives and a binder agent to the charge generating layer 5 and then drying. In this photoconductor, the charge generating material employed is the same as that employed in the photoconductor shown in FIG. 2.

It is preferable that the thickness of the charge generating layer 56 be less than about 5 μm, more preferably less than about 2 μm. It is preferable that the thickness of the charge transporting layer 6 be in the range of about 3 μm to about 50 μm, more preferably in the range of about 5 μm to about 20 μm. In the case where the charge generating layer 5 comprises the charge generating material 3 in the form of fine particles, dispersed in a binder agent, it is preferable that the amount of the charge generating material 3 in the charge generating layer 5 be in the range of about 10 wt.% to about 95 wt.% of the entire weight of the charge generating layer 5, more preferably in the range of about 50 wt.% to about 90 wt.%. Further, it is preferable that the amount of the styryl derivative contained in the charge transporting layer 6 be in the range of about 10 wt.% to about 95 wt.%, more preferably in the range of about 30 wt.% to about 90 wt.% of the total weight of the charge transporting layer 6.

As the electroconductive support material 1 for use in the present invention, a metal plate or metal foil, for example, made of aluminum, a plastic film on which a metal, for example, aluminum, is evaporated, or paper which has been treated so as to be electroconductive, can be employed.

As the binder agent for use in the present invention, condensation resins, such as polyamide, polyurethane, polyester, epoxy resin, polyketone and polycarbonate; and vinyl polymers such as polyvinylketone, polystyrene, poly-N-vinylcarbazole and polyacrylamide, can be used.

Other conventional electrically insulating and adhesive resins can be used as the binder agent in the present invention. When necessary, there can be added to the binder resins a plasticizer, for example, halogenated paraffin, polybiphenyl chloride, dimethylnaphthalene and dibutyl phthalate.

In the above described photoconductors according to the present invention, if necessary, an adhesive layer or a barrier layer can be disposed between the electroconductive support material and the photosensitive layer. The adhesive layer or the barrier layer can be made of, for example, polyamide, nitrocellulose or aluminum oxide. It is preferable that the thickness of the adhesive layer or barrier layer be about 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and, when necessary, the developed image can be transferred to a sheet of paper. The photoconductors according to the present invention have high photosensitivity and excellent flexibility.

Preparation of 4,4'-bis(β-phenylstyryl)triphenylamine (which is a representative example of a styryl derivative) according to the present invention) will now be explained in detail by referring to the following example:

SYNTHESIS EXAMPLE 1.51 g of 4,4'-diformyltriphenylamine and 3.04 g of diethyl 1,1-diphenylmethylphosphonate were dissolved in 20 ml of N,N-dimethyl-formamide. To this mixture, 1.68 g of potassium tert-butoxide was added with the temperature of the reaction mixture maintained in the range of 25° C. to 35° C. After the addition of the potassium tert-butoxide, the reaction mixture was stirred at room temperature for 3 hours and was then diluted with ice water, thereby liberating a precipitate. The precipitate was filtered off, washed with water and dried. The yield was 2.77 g. The thus obtained precipitate was recrystalized from a mixed solvent of ethyl acetate and ethanol, whereby 4,4'-bis(β-phenylstyryl)triphenylamine (Styryl Derivative No. 28 in Table 1) of the following formula (IV) was obtained as light yellow needle-like crystals.

(IV)

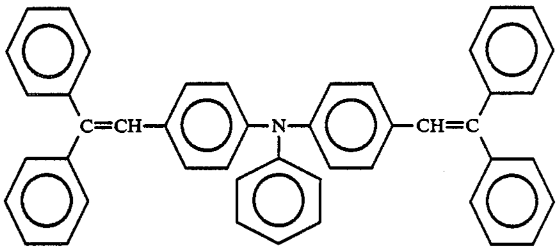

The melting point of the styryl derivative was at 156.0°-157.0° C. The results of the elemental analysis of the thus obtained 4,4'-bis(β-phenylstyryl)triphenylamine were as follows:

| | % C | % H | % N |
|---|---|---|---|
| Found | 91.93 | 5.81 | 2.31 |
| Calculated | 91.80 | 5.87 | 2.33 |

The above calculation was based on the formula for 4,4'-bis(β-phenylstyryl)triphenylamine of $C_{46}H_{35}N$.

| | | |
|---|---|---|
| Mass Spectrometry | m/e | 601 ($M^+$) |

An infrared spectrum of 4,4'-bis(β-phenylstyryl)triphenylamine taken by a KBr pellet is shown in FIG. 1.

Specific preferable examples of styryl derivatives having the formula (I) including the above styryl derivative according to the present invention are listed in the following Table 1:

TABLE 1
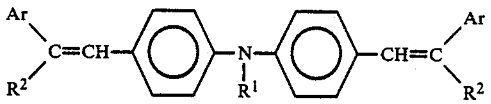
(I)
| Styryl Derivative No. | $R^1$ | $R^2$ | Ar |
|---|---|---|---|
| 1 | $CH_3$ | H | 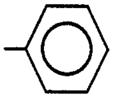 |
| 2 | $C_2H_5$ | H | 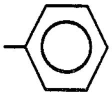 |
| 3 | $C_3H_7(n)$ | H | 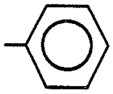 |
| 4 | $CH_3$ | 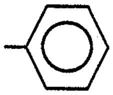 | 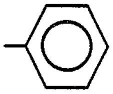 |
| 5 | $CH_3$ | H | 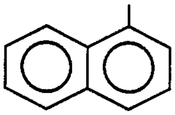 |
| 6 | $CH_3$ | H | 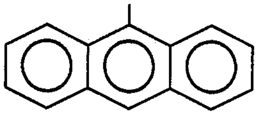 |
| 7 | $CH_3$ | H | 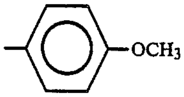 |
| 8 | 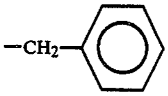 | H | 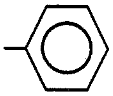 |
| 9 | 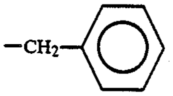 | 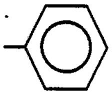 | 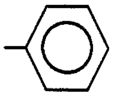 |
| 10 | 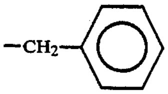 | H | 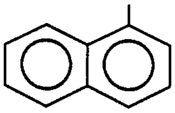 |
| 11 | 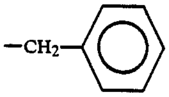 | H | 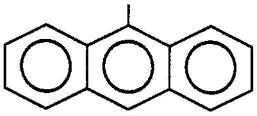 |

TABLE 1-continued
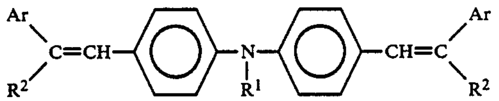
(I)
| Styryl Derivative No. | $R^1$ | $R^2$ | Ar |
|---|---|---|---|
| 12 | 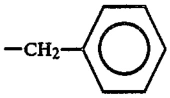 | H | 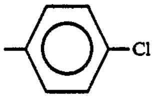 |
| 13 | 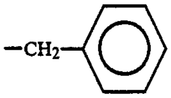 | H | 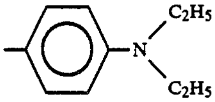 |
| 14 | 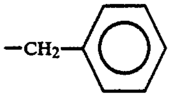 | H | 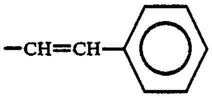 |
| 15 | 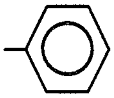 | H | 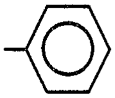 |
| 16 | 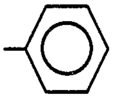 | H | 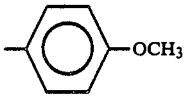 |
| 17 | 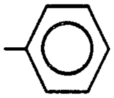 | H | 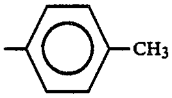 |
| 18 | 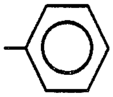 | H | 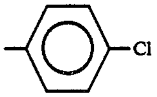 |
| 19 | 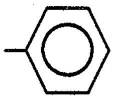 | H | 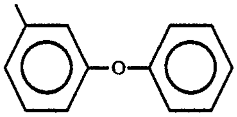 |
| 20 | 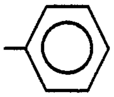 | H | 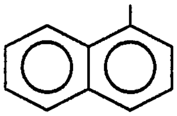 |
| 21 | 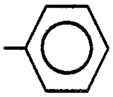 | H | 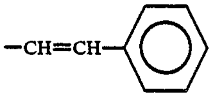 |
| 22 | 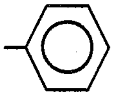 | H | 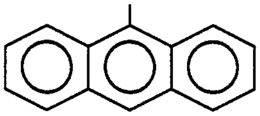 |

TABLE 1-continued
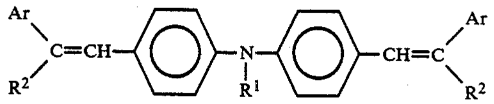
(I)
| Styryl Derivative No. | $R^1$ | $R^2$ | Ar |
|---|---|---|---|
| 23 | 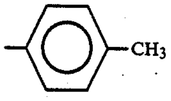 | H | 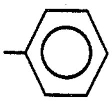 |
| 24 | 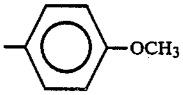 | H | 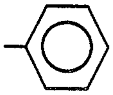 |
| 25 | 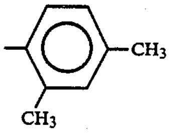 | H | 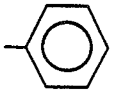 |
| 26 | 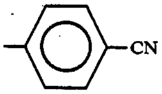 | H | 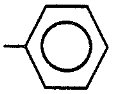 |
| 27 | 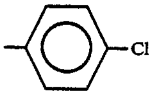 | H | 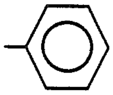 |
| 28 | 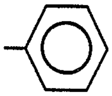 | 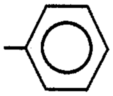 | 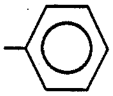 |
| 29 | 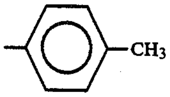 | 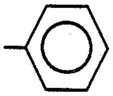 | 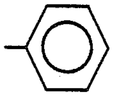 |
| 30 | 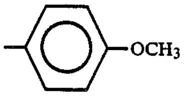 | 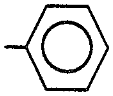 | 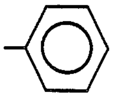 |
| 31 | 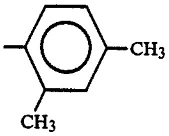 | 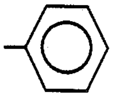 | 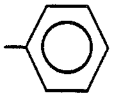 |
| 32 | 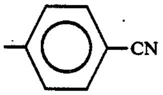 | 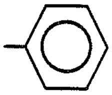 | 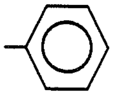 |
| 33 | 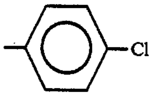 | 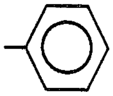 | 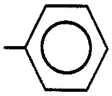 |

TABLE 1-continued

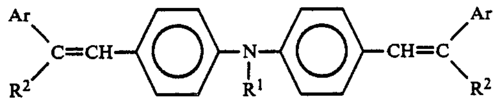

(I)

| Styryl Derivative No. | $R^1$ | $R^2$ | Ar |
|---|---|---|---|
| 34 | 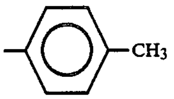 | H | 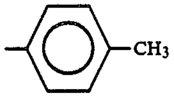 |
| 35 | 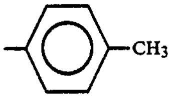 | H | 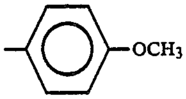 |
| 36 | 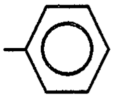 | 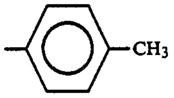 | 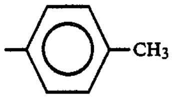 |
| 37 | 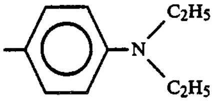 | 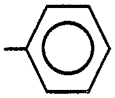 | 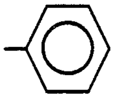 |
| 38 | 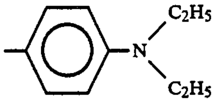 | H | 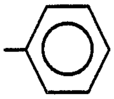 |
| 39 | 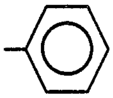 | $CH_3$ | 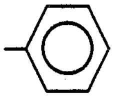 |
| 40 | 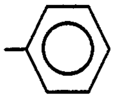 | 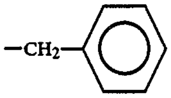 | 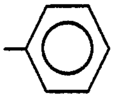 |
| 41 | 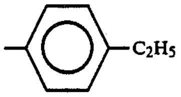 | 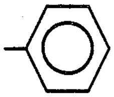 | 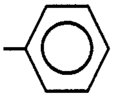 |
| 42 | 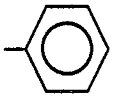 | H | 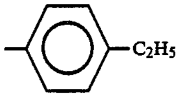 |
| 43 | 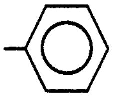 | H | 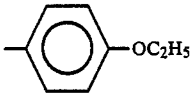 |

Preparation of embodiments of an electrophotographic photoconductor according to the present invention will now be explained in detail by referring to the following examples:

EXAMPLE P-1

The following components were ground and dispersed in a ball mill to prepare a charge generating layer formation liquid:

| | Parts by Weight |
|---|---|
| Diane Blue (C.I. Pigment Blue 25, C.I. 21180, a charge generating pigment) | 76 |
| 2% tetrahydrofuran solution of a polyester resin (Vylon 200 made by Toyobo Co., Ltd.) | 1,260 |

-continued

| | Parts by Weight |
|---|---|
| Tetrahydrofuran | 3,700 |

The thus prepared charge generating layer formation liquid was applied by a doctor blade to the aluminum-evaporated surface of an aluminum-evaporated polyester base film, which served as an electroconductive support material, so that a charge generating layer, with a thickness of about 1 μm when dried at room temperature, was formed on the electroconductive support material.

The following components were then mixed and dissolved, whereby a charge transporting layer formation liquid was prepared:

| | Parts by Weight |
|---|---|
| 4,4'-bis(β-phenylstyryl)triphenylamine (Styryl Derivative No. 28 in Table 1, prepared in Synthesis Example) | 2 |
| Polycarbonate resin (Panlite K 1300 made by Teijin Limited.) | 2 |
| Tetrahydrofuran | 16 |

The thus prepared charge transporting layer formation liquid was applied to the aforementioned charge generating layer by a doctor blade and was dried at 80° C. for 2 minutes and then at 105° C. for 5 minutes, so that a charge transporting layer with a thickness of about 20 μm was formed on the charge generating layer; thus, an electrophotographic photoconductor No. 1 according to the present invention was prepared.

The electrophotographic photoconductor No. 1 was charged negatively in the dark under application of −6 kV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 4.5 lux, and the exposure $E_{\frac{1}{2}}$ (lux·seconds) required to reduce the initial surface potential Vpo (V) 1 to ½ the initial surface potential Vpo (V) was measured. The results showed that Vpo (V)= −1210 and $E_{\frac{1}{2}}$ = 1.5 lux·seconds.

EXAMPLES P-2 THROUGH P-27

Example P-1 was repeated except that the charge generating material and the charge transporting material (Styryl Derivative No. 28 in Table 1) employed in Example P-1 were respectively replaced by the charge generating materials and the charge transporting materials (styryl derivatives) listed in Table 2, whereby electrophotographic photoconductors No. 2 through No. 27 according to the present invention were prepared.

Vpo and $E_{\frac{1}{2}}$ of each electrophotographic photoconductor are shown in Table 3.

TABLE 2
| Photoconductor No. | Charge Generating Material | | Charge Transporting Material Styryl Derivative No. in Table 1 |
|---|---|---|---|
| 1 | 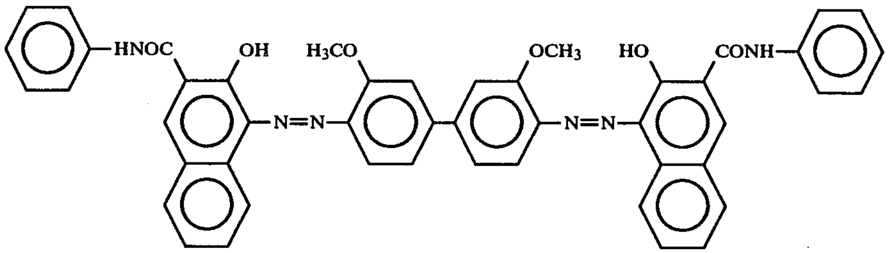 | (CG-1) | 28 |
| 2 | 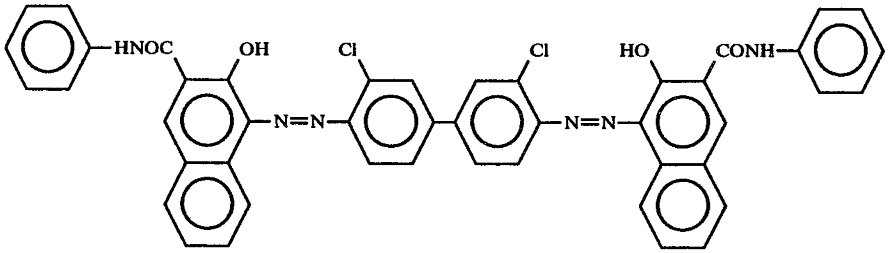 | (CG-2) | 28 |
| 3 | 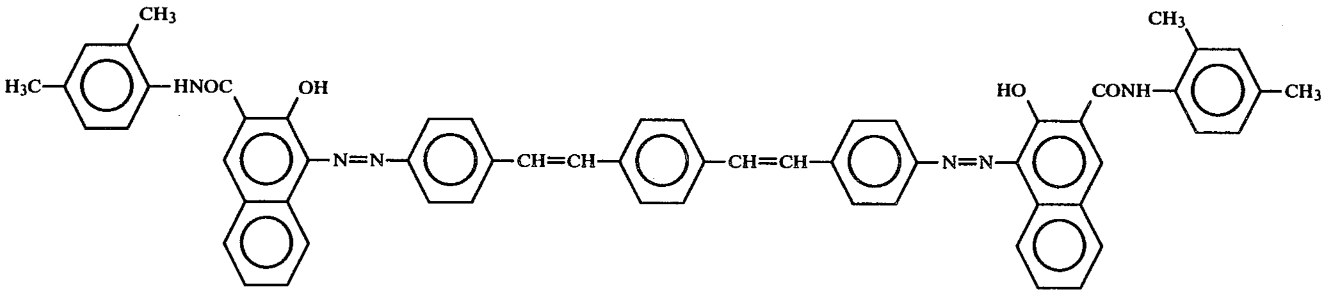 | (CG-3) | 28 |

TABLE 2-continued
| Photoconductor No. | Charge Generating Material | | Charge Transporting Material Styryl Derivative No. in Table 1 |
|---|---|---|---|
| 4 | 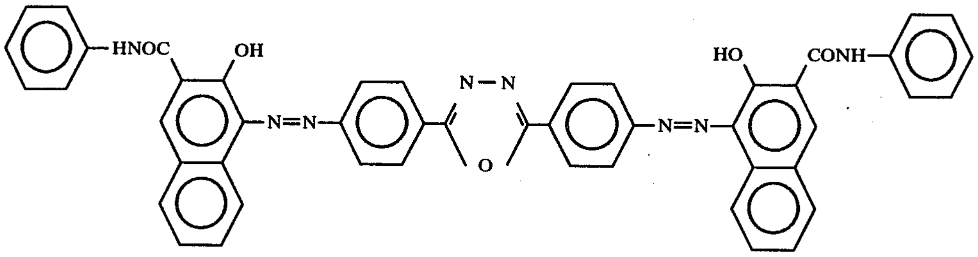 | (CG-4) | 28 |
| 5 | 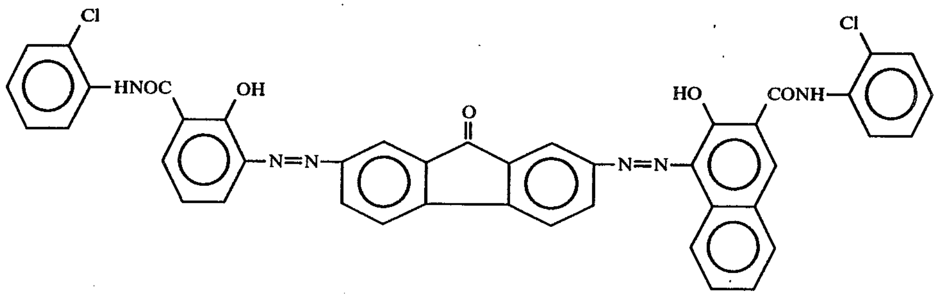 | (CG-5) | 28 |

TABLE 2-continued
| Photoconductor No. | Charge Generating Material | | Charge Transporting Material Styryl Derivative No. in Table 1 |
|---|---|---|---|
| 6 | 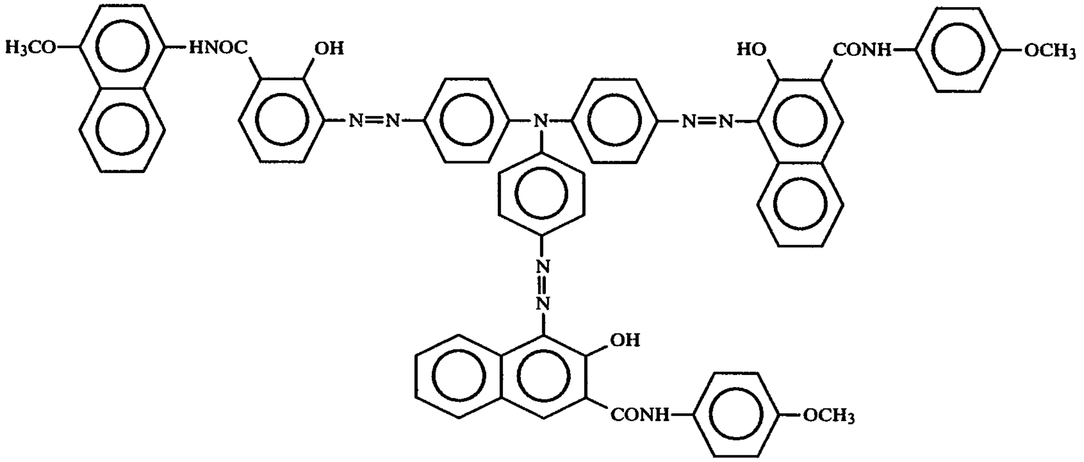 | (CG-6) | 28 |
| 7 | β-type Copper Phthalocyanine | | 28 |
| 8 | 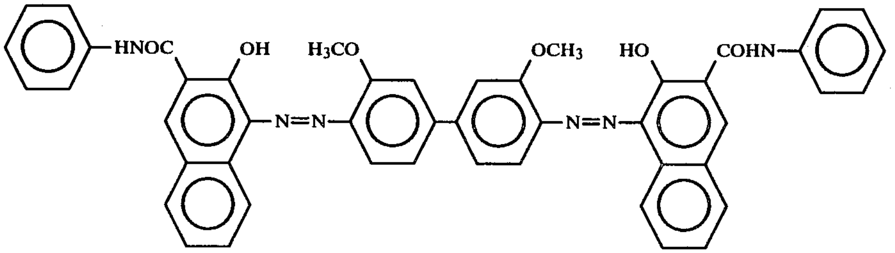 | (CG-1) | 29 |

TABLE 2-continued
| Photoconductor No. | Charge Generating Material | Charge Transporting Material Styryl Derivative No. in Table 1 |
|---|---|---|
| 9 | 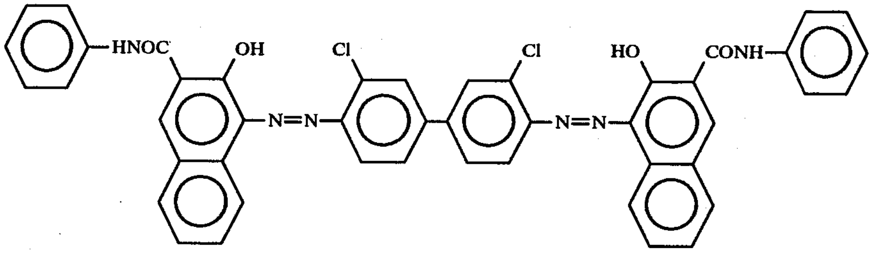 (CG-2) | 29 |
| 10 | CG-3 | 29 |
| 11 | CG-5 | 29 |
| 12 | CG-3 | 30 |
| 13 | CG-5 | 30 |
| 14 | CG-3 | 15 |
| 15 | CG-5 | 15 |
| 16 | CG-3 | 42 |
| 17 | CG-5 | 42 |
| 18 | CG-3 | 43 |
| 19 | CG-5 | 43 |
| 20 | CG-3 | 14 |
| 21 | CG-5 | 14 |
| 22 | CG-3 | 2 |
| 23 | CG-5 | 2 |
| 24 | CG-3 | 8 |
| 25 | CG-5 | 8 |
| 26 | CG-3 | 9 |
| 27 | CG-5 | 9 |

EXAMPLE P-28

Selenium was vacuum-evaporated with a thickness of about 1.0 μm on an about 300 μm thick aluminum plate so that a charge generating layer was formed on the aluminum plate.

A charge transporting layer formation liquid was prepared by mixing and dispersing the following components:

| | Parts by Weight |
|---|---|
| 4,4'-bis(β-phenylstyryl)triphenylamine (Styryl Derivative No. 28 in Table 1) | 2 |
| Polyester resin (Polyester Adhesive 49000 made by Du Pont Co.) | 3 |
| Tetrahydrofuran | 45 |

The thus prepared charge transporting layer formation liquid was applied to the aforementioned selenium charge generating layer by a doctor blade, dried at room temperature and then dried under reduced pressure, so that a charge transporting layer about 10 μm thick was formed on the charge generating layer; thus, an electrophotographic photoconductor No. 28 according to the present invention was prepared.

Vpo and $E_{1/2}$ were measured. The results showed that Vpo = −760 V and $E_{1/2}$ = 3.1 lux·seconds.

EXAMPLE P-29

A perylene pigment C.I. Vat Red 23 (C.I. 71130) of the following formula was vacuum-evaporated with a thickness of about 0.3 μm on an about 300 μm thick aluminum plate so that a charge generating layer was formed:

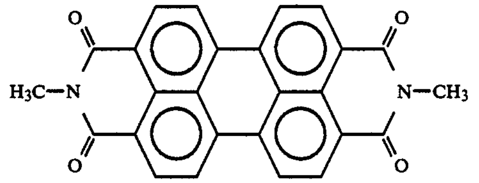

A charge transporting layer formation liquid was prepared by mixing and dispersing the following components:

| | Parts by Weight |
|---|---|
| Styryl Derivative No. 29 in Table 1 | 2 |
| Polyester resin (Polyester Adhesive 49000 made by Du Pont Co.) | 3 |
| Tetrahydrofuran | 45 |

The thus prepared charge transporting layer formation liquid was applied to the aforementioned perylene pigment charge generating layer by a doctor blade, dried at room temperature and then dried under reduced pressure, whereby a charge transporting layer about 10 μm thick was formed on the charge generating layer; thus, an electrophotographic photoconductor No. 29 according to the present invention was prepared.

Vpo and $E_{1/2}$ were measured. The results showed that Vpo = −1150 V and $E_{1/2}$ = 4.0 lux·seconds.

EXAMPLE P-30

One part by weight of Diane Blue (C.I. Pigment Blue 25, C.I. 21180) was added to 158 parts by weight of tetrahydrofuran, and the mixture was ground and dispersed in a ball mill. To this mixture, 12 parts by weight of Styryl Derivative No. 28 in Table 1 and 18 parts by weight of a polyester resin (Polyester Adhesive 49000 made by Du Pont Co.) were added and mixed, whereby a photosensitive layer formation liquid was prepared.

The thus prepared photosensitive layer formation liquid was applied to an aluminum-evaporated polyester film by a doctor blade and was dried at 100° C. for 30 minutes, so that a photosensitive layer having a thickness of about 16 μm was formed on the aluminum-evaporated polyester film, thus, an electrophotographic photoconductor No. 30 according to the present invention was prepared.

The electrophotographic photoconductor No. 30 was charged positively in the dark under application of +6 kV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 4.5 lux, so that the exposure $E_{178}$ (lux·seconds) required to reduce the initial surface potential Vpo (V) to ½ the initial surface potential Vpo (V) was measured. The results showed that Vpo (V) = +1030 and $E_{1/2}$ = 2.5 lux·seconds.

The charge generating material, the charge transporting material, $V_{po}$ and $E_{1/2}$ of each of the electrophotographic photoconductors No. 1 through No. 30 are summarized in the following Table 3:

TABLE 3

| Photo-Conductor No. | Charge Generating Material | Charge Transporting Material No. (Styryl Derivative) | $V_{po}$ (V) | $E_{1/2}$ (lux · seconds) |
|---|---|---|---|---|
| 1 | CG-1 | 28 | −1210 | 1.5 |
| 2 | CG-2 | 28 | −970 | 1.4 |
| 3 | CG-3 | 28 | −1090 | 1.0 |
| 4 | CG-4 | 28 | −1140 | 1.9 |
| 5 | CG-5 | 28 | −970 | 0.7 |
| 6 | CG-6 | 28 | −1100 | 1.3 |
| 7 | β-type Copper Phthalocyanine | 28 | −910 | 1.4 |
| 8 | CG-1 | 29 | −1110 | 1.5 |
| 9 | CG-2 | 29 | −980 | 1.2 |
| 10 | CG-3 | 29 | −1200 | 1.1 |
| 11 | CG-5 | 29 | −790 | 0.6 |
| 12 | CG-3 | 30 | −1070 | 0.9 |
| 13 | CG-5 | 30 | −920 | 0.7 |
| 14 | CG-3 | 15 | −1000 | 1.0 |
| 15 | CG-5 | 15 | −870 | 1.1 |
| 16 | CG-3 | 42 | −990 | 0.9 |
| 17 | CG-5 | 42 | −940 | 0.7 |
| 18 | CG-3 | 43 | −1120 | 1.2 |
| 19 | CG-5 | 43 | −1010 | 0.8 |
| 20 | CG-3 | 14 | −1210 | 1.6 |
| 21 | CG-5 | 14 | −1100 | 1.4 |
| 22 | CG-3 | 2 | −970 | 1.8 |
| 23 | CG-5 | 2 | −980 | 1.4 |
| 24 | CG-3 | 8 | −1130 | 1.3 |
| 25 | CG-5 | 8 | −960 | 1.5 |
| 26 | CG-3 | 9 | −1200 | 1.6 |
| 27 | CG-5 | 9 | −1000 | 1.2 |
| 28 | Se | 28 | −760 | 3.1 |
| 29 | Perylene Pigment | 29 | −1150 | 4.0 |
| 30 | CG-1 | 28 | +1030 | 2.5 |

Each of the electrophotographic photoconductors prepared in Examples P-1 through P-29 was negatively charged, while the electrophotographic photoconductor prepared in Example P-30 was positively charged, by a commercially available copying machine, so that latent electrostatic images were formed on each photoconductor and were developed with a dry type developer. The developed images were transferred to a high quality transfer sheet and were fixed to the transfer sheet. As a result, clear images were obtained from each of the electrophotographic photoconductors.

When a wet type developer was used instead of the dry type developer, clear images were also obtained from each of the electrophotographic photoconductors.

The electrophotographic photoconductors according to the present invention have high photosensitivity and excellent durability against heat and mechanical shocks and can be prepared inexpensively.

What is claimed is:

1. A styryl derivative of the formula

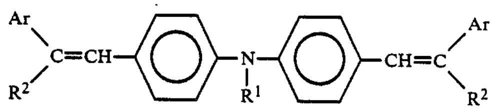

wherein $R^1$ is selected from the group consisting of an alkyl group, a substituted alkyl group, an aryl group and a substituted aryl group; $R^2$ is selected from the group consisting of hydrogen, a phenyl group and a substituted aryl group; and Ar represents an phenyl group or a substituted aryl group.

2. A styryl derivative as claimed in claim 1, wherein said aryl group is selected from the group consisting of a phenyl group, a styryl group, a biphenylyl group, a naphthyl group and an anthryl group; and said substituted aryl group have at least one substituent selected from the group consisting of an alkyl group, an alkoxy group, an aryloxy group, halogen, a dialkylamino group, a hydroxy group, a carboxy group and esters thereof, a nitro group, an acetyl group and a cyano group.

* * * * *